United States Patent [19]

Oakes

[11] Patent Number: 5,384,242
[45] Date of Patent: Jan. 24, 1995

[54] DIAGNOSTIC KIT, PRIMER COMPOSITION AND THEIR USE FOR REPLICATION OR DETECTION OF NUCLEIC ACIDS

[75] Inventor: Fred T. Oakes, Rochester, N.Y.

[73] Assignee: Eastman Kodak Company, Rochester, N.Y.

[21] Appl. No.: 895,759

[22] Filed: Jun. 9, 1992

Related U.S. Application Data

[63] Continuation of Ser. No. 339,436, Apr. 17, 1989, abandoned.

[51] Int. Cl.⁶ .................. C12Q 1/68; C12P 19/34; C07H 21/04; C12N 15/00
[52] U.S. Cl. .................. 435/6; 435/91.2; 536/24.33; 935/77; 935/78
[58] Field of Search ............. 435/6, 91, 91.2; 536/27, 24.33; 935/77, 78

[56] References Cited

U.S. PATENT DOCUMENTS

| | | | |
|---|---|---|---|
| 4,089,747 | 5/1978 | Bruschi | 195/99 |
| 4,683,195 | 1/1987 | Mullis et al. | 435/6 |
| 4,683,202 | 7/1989 | Mullis | 435/91 |
| 4,988,617 | 1/1991 | Landegren et al. | 435/6 |

FOREIGN PATENT DOCUMENTS 0297379  1/1989  European Pat. Off.

OTHER PUBLICATIONS

Clavel et al, Nature, vol. 324, Dec. 1986, pp. 691–695.
Saiki et al, Science, vol. 239, Jan. 29, 1988, pp. 487–491.
Matthews et al, Anal. Biochem, vol. 169, Feb. 1988, pp. 1–25.
Mullis et al, Cold Spring Harbor Symposia, 1986, Cold Spring Harbor Lab, pp. 263–273.

Primary Examiner—Mindy B. Fleisher
Attorney, Agent, or Firm—James L. Tucker

[57] ABSTRACT

Amplification, replication or detection of a predetermined target nucleic acid can be carried out using a unique primer composition. This composition comprises and aqueous mixture of a first oligonucleotide primer which is substantially complementary to a first nucleic acid sequence of the target, but which is suspected of having one or more mismatches with the target at or near its 3' end. Also included in the composition is one or more additional primers which are complementary to a nucleic acid sequence of the target. This sequence is either: (i) inclusive of only a portion of the first nucleic acid sequence, (ii) immediately adjacent to the first nucleic acid sequence, or (iii) removed from the first sequence by one or more bases, but which additional primer is capable of forming a primer extension product complementary to the first sequence. These composition components can be supplied as part of a diagnostic test kit which can include other regents if desired.

32 Claims, 4 Drawing Sheets

DIAGNOSTIC KIT, PRIMER COMPOSITION AND THEIR USE FOR REPLICATION OR DETECTION OF NUCLEIC ACIDS

This is a continuation of application Ser. No. 339,436, filed Apr. 17, 1989, abandoned.

FIELD OF THE INVENTION

The present invention relates to a primer composition and diagnostic test kit, and to their use for replication or detection of a target nucleic acid in a test specimen. The present invention can be used in various medical and research studies, forensic investigations and diagnostic procedures, such as for the detection of genetic disorders or infectious diseases.

BACKGROUND OF THE INVENTION

Nucleic acid probe technology has developed rapidly in recent years as researchers have discovered its value for detection of various diseases, organisms or genetic features which are present in very small quantities in a test sample. The use of probes is based upon the concept of complimentarily. For example, DNA is double-stranded, the strands bound to each other by hydrogen bonds between complementary nucleotides (also known as nucleotide pairs).

The DNA complex is normally stable, but the strands can be separated (or denatured) by conditions which disrupt the hydrogen bonding. The released single strands will reassociate only with another strand having a complementary sequence of nucleotides. This hybridization process can occur in solution or on a solid substrate. RNA is usually single-stranded. It can also hybridize with another strand or portion thereof which has a complementary sequence of nucleotides.

A target nucleic acid sequence of the DNA or RNA of a target organism or cell may be only a small portion of the total strand, so that it is very difficult to detect its presence using most known labeled probes. Much research has been carried out to overcome this problem including improvements in probe sensitivity and synthesis of nucleic acids.

A significant advance in the art is the process described in U.S. Pat. No. 4,683,202 (issued Jul. 28, 1987 to Mullis). Without going into extensive detail regarding that process, it is an amplification technique wherein primers are hybridized to nucleic acid templates in the presence of a polymerization agent (such as a polymerase) and four nucleotide triphosphates, and extension products are formed from the primers. These products are denatured and used as templates in a cycling reaction which amplifies the number and amount of existing nucleic acids to facilitate their subsequent detection. The amplification process of Mullis can be carried out cyclically as many times as desired to produce a larger quantity of detectable material from a small amount of target nucleic acid sequence.

In the process of U.S. Pat. No. 4,683,202, two primers are used for each strand of the target nucleic acid to be amplified. In the best case for amplification, the nucleic acid sequence to be amplified is completely complementary with the primer, at least near the 3' end of the target sequence. Thus, only one primer per strand is needed for effective amplification. It is known from the Mullis patent that where the target sequence is not entirely known, at least at the 3' end, a collection of primers can be used having all possible codon variations in order to have at least one primer which is completely complementary. Such a primer is said to have 100% "homology" with the end of the strand to be amplified.

This procedure may sometimes accomplish the amplification process desired, but it may be inefficient or ineffective in other instances. The preparation of the collection of random primers is wasteful and leads to the use of competitive non-extending primers. Moreover, when the uncertainty of the target nucleotide sequence is greater, the collection of primers needed is greatly enlarged.

Mismatches between target sequence and primers cannot be entirely avoided, particularly when the target sequence cannot be identified completely. In other instances, such as the detection of provital DNA from retroviruses, the target nucleic acid is highly variable, and complete identity cannot be maintained. With HIV-I, a variety of sequences in the genome produces a viable virus. Base substitutions are known to occur at random and frequent intervals over the entire genome. Thus, isolates are likely to have provital DNA which have different nucleic acid sequences.

Such mismatches will considerably reduce the efficiency of amplification by primers. In other words, mismatches lead to a slowing down of the amplification process because the kinetics of priming and primer extension have changed [see for example, an article by Tinoco, Jr., *Proc. Nat. Acad. Sci.(USA)*, 85, 6252 (1988)]. In the worst case, no amplification will occur as the primer fails to attach to the target, or if it attaches, formation of an extension product is inhibited (that is, the primer "misfires").

It would be desirable to have an efficient means for amplifying nucleic acid sequences even if there are suspected mismatches between the target sequence and a known primer to that sequence.

SUMMARY OF THE INVENTION

The problems noted above are overcome with the use of a primer composition useful for amplification or replication of a predetermined target nucleic acid, the composition comprising an aqueous mixture of:

a) a first oligonucleotide primer which is substantially complementary to a first specific nucleic acid sequence of the target nucleic acid, and b) at least one additional oligonucleotide primer which is at least substantially complementary to a nucleic acid sequence of the target acid which is either:
  i) inclusive of only a portion of the first nucleic acid sequence,
  ii) immediately adjacent to the first nucleic acid sequence, or
  iii) removed from the first nucleic acid sequence by one or more nucleotide bases, but which additional primer is capable of forming a primer extension product complementary to the first specific nucleic acid sequence.

This invention also provides a diagnostic test kit useful for amplification or replication of a predetermined target nucleic acid comprising:

a) the first primer described above, and b) at least one additional primer as described above.

A method for the replication of a predetermined target nucleic acid comprises:

A. preparing a specimen containing the predetermined target nucleic acid for replication, B. contacting the prepared specimen with the primer composition described above so as to form a mixture of hybridized products of the primers and target nucleic acid, and C. forming a first primer extension product in at least one of the hybridized products, and priming and extending the first primer extension product.

Further, a method for the detection of a predetermined target nucleic acid comprises:

A. contacting a specimen suspected of containing the target nucleic acid with the primer composition described above so as to form a mixture of hybridized products of the primers and target nucleic acid, B. forming a first primer extension product in at least one of the hybridized products, priming and extending the first primer extension product, and amplifying the first primer extension product, C. separating the resulting primer extension products and contacting them with a detectable oligonucleotide probe to form a detectable complementary product, and D. determining the detectable complementary product as an indication of the presence of the target nucleic acid in the specimen.

The present invention provides a means for rapidly and accurately replicating, amplifying or detecting nucleic acid sequences which are present in very small quantities in a test specimen. Moreover, these processes can be carried out even if there is a mismatch in complimentarily between the target sequence and a primer which the operator considers likely to prime that sequence. This will make the processes considerably more efficient in detecting genomic sequences which are variant from isolate to isolate, such as with retroviruses.

These advantages are achieved by using a primer composition that includes a first primer which may or may not have a mismatch with the target sequence at or near the 3'-end of the primer. If there is no mismatch, the priming and later processes are carried out efficiently. However, where there is one or more mismatches, the first primer may still prime the sequence, but extension product formation may be delayed or completely inhibited depending upon where the mismatches occur. The present invention overcomes this problem by including in the composition one or more additional primers, at least one of which will properly prime and provide extension products as desired. These additional primers may contain a different number of nucleotides as compared to the first primer but are still related to it in a unique way, as described in more detail below. This set of primers in the primer composition are defined herein as a set of "homologous" primers.

DETAILED DESCRIPTION OF THE INVENTION

Figure 1:
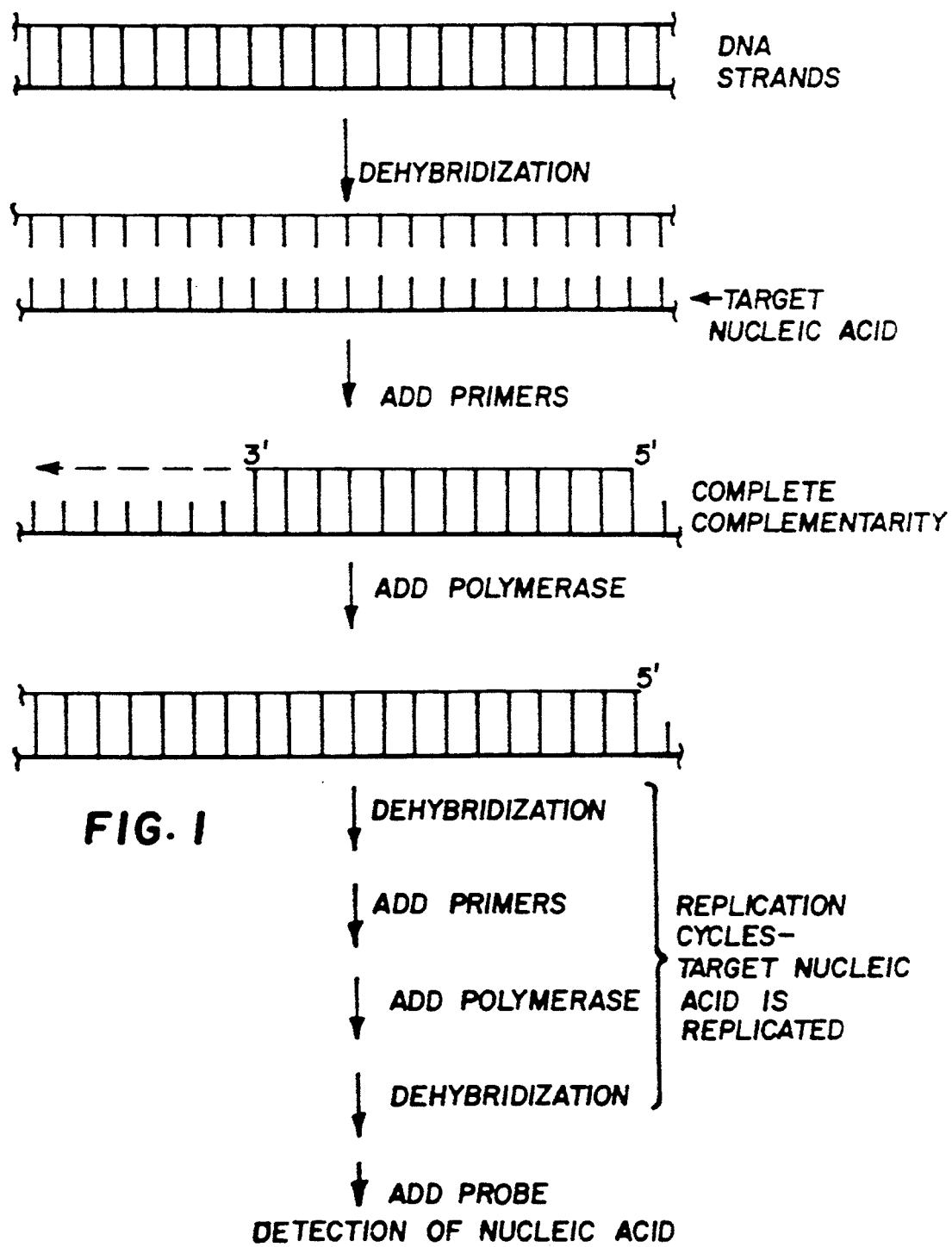
FIG. 1 is a schematic diagram showing a conventional priming and amplification technique directed against a target nucleic acid.

The present invention is directed to the replication, amplification or detection of one or more specific nucleic acid sequences present in one or more target nucleic acids in a test specimen. Such samples can include cellular or viral material, hair, body fluids or other materials containing genetic DNA or RNA which can be detected. While the primary purpose of detection would be diagnostic in nature, the invention could also be used to improve the efficiency of cloning DNA or messenger RNA, or for obtaining large amounts of the desired sequence from a mixture of nucleic acids resulting from chemical synthesis.

The present invention is especially useful when combined with a chain reaction for producing, in exponential quantities relative to the number of reaction steps involved, at least one specific nucleic acid sequence. The product will be a discrete nucleic acid duplex with termini corresponding to the ends of the specific primers employed. Any source of nucleic acid, purified or not, can be utilized as the starting material provided it contains or is suspected of containing the specific nucleic acid sequence targeted for detection. A mixture of nucleic acids can be employed if desired. The sequence to be duplicated can be a fragment or the entire nucleic acid. Moreover, more than one nucleic acid sequence can be amplified simultaneously by using a specific set of primers and labeled probes for each sequence to be amplified. The sequences can be in the same or different nucleic acids.

Nucleic acids can be obtained from various sources including plasmids, naturally occurring DNA or RNA from any source (such as bacteria, yeast, viruses, plants and higher animals, humans). It may be extracted from various tissues including blood, peripheral blood mononuclear cells (PBMC), tissue material or other sources known in the art using known procedures. The present invention is particularly useful for the detection of nucleic acid sequences found in viruses or cells of any organism, such as in genomic DNA, bacterial DNA, viral RNA, or DNA or RNA found in bacterial or viral infected cells. This invention is particularly useful for the detection of viral DNA from cells infected by HIV-I or other retroviruses.

As used herein in referring to primers, probes or oligomer fragments to be detected, the term "oligonucleotide" refers to a molecule comprised of two or more deoxyribonucleotides or ribonucleotides, and preferably more than three. The exact size is not critical but depends upon many factors including the ultimate use or function of the oligonucleotide. The oligonucleotide may be derived synthetically or by other methods known in the art.

The term "primer" refers to an oligonucleotide, whether naturally occurring or synthetically produced, which is capable of acting as a point of initiation of synthesis when placed under conditions in which synthesis of a primer extension product complementary to a nucleic acid strand is induced. Such conditions include the presence of nucleotides (such as the four standard deoxyribonucleoside triphosphates) and an agent for polymerization such as a DNA polymerase, and suitable temperature and pH.

The composition of this invention has a first oligonucleotide primer which is substantially complementary to a first nucleic acid sequence of the target nucleic acid. By "substantially complementary" is meant that there are a sufficient number of bases on the primer that match with the corresponding bases in the nucleic acid sequence that the primer will hybridize with that sequence. It does not mean, however, that every base pair will match. In fact, this invention is intended to address the problems that arise when there are one or more mismatches, especially at or near the 3' end of the first primer where it is desired that primer extension will occur. It is understood that the present invention also works well when there are no mismatches. One can not always predict where such mismatches may occur.

In the practice of this invention, any of the primers used (both the first and additional ones) can contain a double-stranded, labeled nucleic acid region adjacent to a single-stranded region. The single-stranded region contains a nucleic acid sequence which is sufficiently complementary to the template strand to hybridize therewith. The double-stranded region, or tail, of the primer can be labeled with a detectable moiety which is capable of producing a detectable signal or which is useful in capturing or immobilizing the extension product. Further details regarding such primers, useful labels, methods of preparation are available in U.S. Ser. No. 076,394 (filed Jul. 22, 1987 by Watson and Levenson) abandoned.

In other and preferred embodiments, the primers are entirely single-stranded. Preferably, the primers are single-stranded oligodeoxyribonucleotides. The exact size of each primer will vary depending upon the use contemplated, the complexity of the target sequence, reaction temperature and the source of the primer. Generally, the primers used in this invention will have from 15 to 50 nucleotides, and preferably, it has from 20 to 30 nucleotides.

The primers used in the present invention are selected to be "substantially" complementary to the different strands of each specific sequence to be amplified. This means that they must be sufficiently complementary to hybridize with their respective strands to form the desired hybridized products. In an ideal situation, the primer would have exact complementarity to the target nucleic acid. However, it many situations, exact complementarity is not possible or likely, and one or more mismatches may exist which will either cause the primer to hybridize poorly, or if primed, to form extension products either very inefficiently (that is, at a slow rate of adding the first base to the primer during extension) or not at all.

Primers useful herein can be obtained from a number of sources or prepared using known techniques and equipment, including for example, an ABI DNA Synthesizer (available from Applied Biosystems) or a Biosearch 8600 Series or 8800 Series Synthesizer (available from Milligen-Biosearch, Inc.) and known methods for their use. Naturally occurring primers isolated from biological sources are also useful (such as restriction endonuclease digests).

The practice of this invention requires the use of a primer composition which includes the first primer described above, and one or more additional oligonucleotide primers. These additional primers are substantially complementary to a nucleic acid sequence which is related to the nucleic acid sequence for the first primer in a certain way. In other words, the first primer is complementary to a first sequence. If there are four additional primers, for example, they are substantially complementary to four additional nucleic acid sequences which are related to the first sequence in a certain manner (described below).

These additional primers can be derived or prepared as described above, and have appropriate size for the desired purposes. In some embodiments (described in more detail below), the size of the primers may be specifically designed in relation to the first primer.

The nucleic acid sequences to which the additional primers are complementary are related to the nucleic acid sequence of the first primer in one or more of the following relationships:

i) inclusive of only a portion of the first nucleic acid sequence, ii) immediately adjacent to the first nucleic acid sequence, or iii) removed from the first nucleic acid sequence by one or more nucleotide bases, but which additional primer is capable of forming a primer extension product complementary to the first specific nucleic acid sequence.

It is contemplated also that a multiplicity of additional primers can be used in the practice of the invention, including one or more of each category (i)–(iii) noted above.

These relationships of the additional primer(s) to the first primer can be better understood by reference to FIGS. 1–6. In all of these drawings, nucleic acids are simply represented by straight horizontal lines (for the nucleotides) having indefinite lengths, and individual bases extending from the nucleic acid backbone represented by vertical lines. Such vertical lines can represent individual bases or base pairs (where double strands or primed single strands are shown). The primers are similarly represented with dotted line arrows to represent the direction of primer extension from the 3' end. It should be noted first that FIG. 1 is a highly simplified schematic illustration of the known amplification process described in more detail in U.S. Pat. No. 4,683,202 (noted above), and incorporated herein by reference. That process generally requires only one primer for each strand which is substantially complementary to the nucleic acid sequence of interest in order to obtain rapid and efficient amplification.

FIGS. 2–6 illustrate several embodiments of the present invention. It is to be understood that other embodiments are possible and included within the scope of this invention. Moreover, the illustrated target nucleic acid sequences and primers are shown to be relatively short, but they are for illustration only, as they may be of any suitable length of nucleotide bases.

Figure 2:
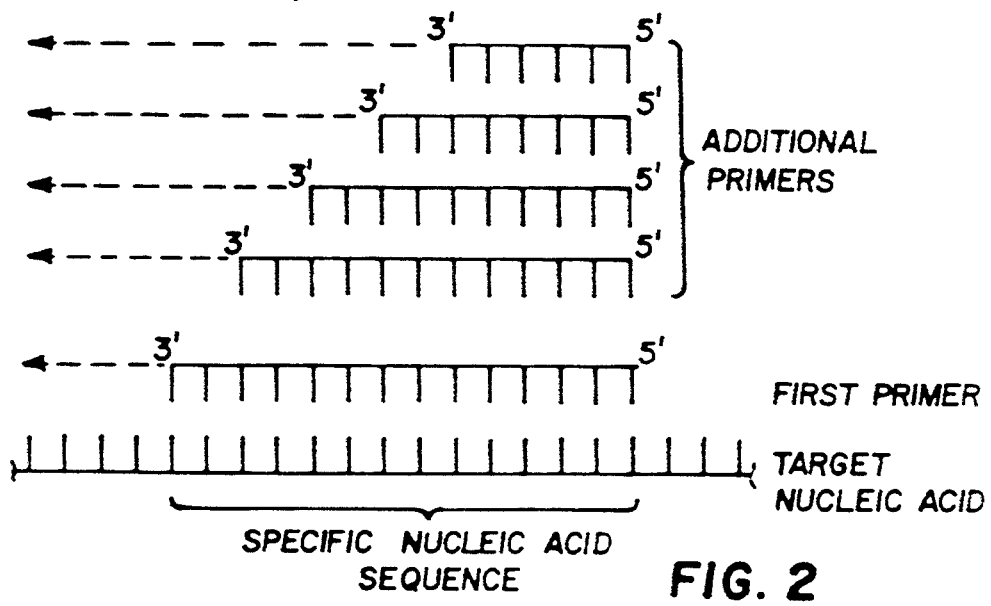
FIG. 2 is a schematic diagram showing an embodiment of this invention as described in more detail on page 12 below.

FIG. 2 shows an embodiment of category (i), noted above, in which the additional primers are complementary with only a portion of the first nucleic acid sequence. In this case, the additional primers have the same base sequence near their 5' ends as the first primer, but vary in length by two bases between each other. This base variation is arbitrary in this illustration. They could as likely vary by one, three or another number of bases. The base at the 5' end of each primer is the same in this embodiment. In a preferred embodiment, the primers are complementary to nucleic acid sequences which are entirely within the first sequence.

Figure 3:
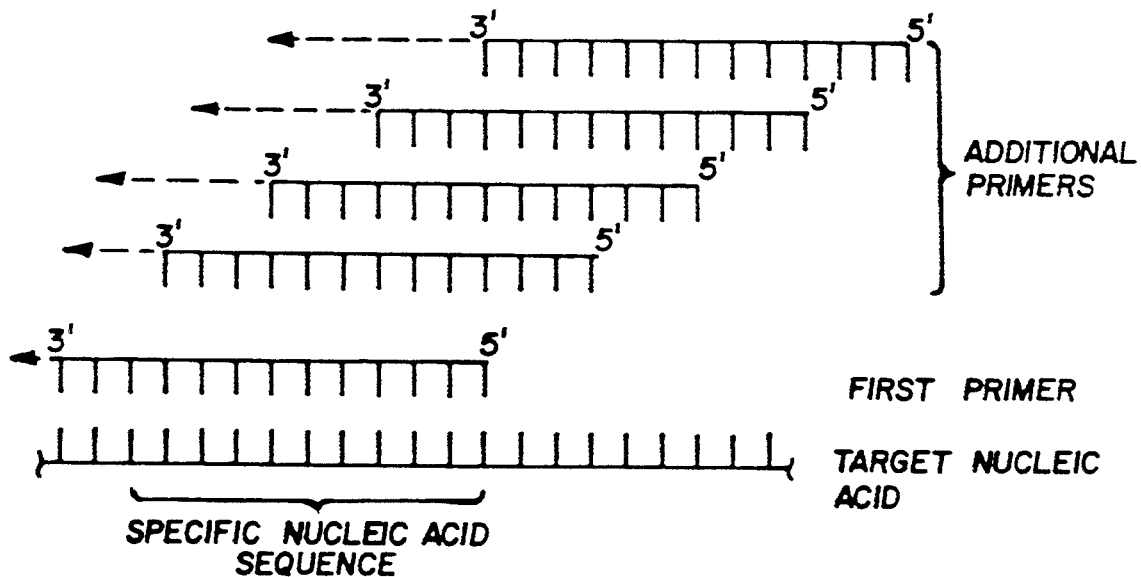
FIG. 3 is a schematic diagram showing another embodiment of this invention as described in more detail on page 12 below.

FIG. 3 shows another embodiment of category (i), noted above, wherein the additional primers have the same length as the first primer, but they are complementary with only a portion of the first nucleic acid sequence. Moreover, they overlap the first primer by at least one base. The illustrated additional primers are shown as being shifted from each other by three bases, but they could be similarly staggered by any other number of bases as long as there was overlap of at least one base with the first primer. In a preferred embodiment, each additional primer is complementary to a sequence which is shifted by a single base.

Figure 4:
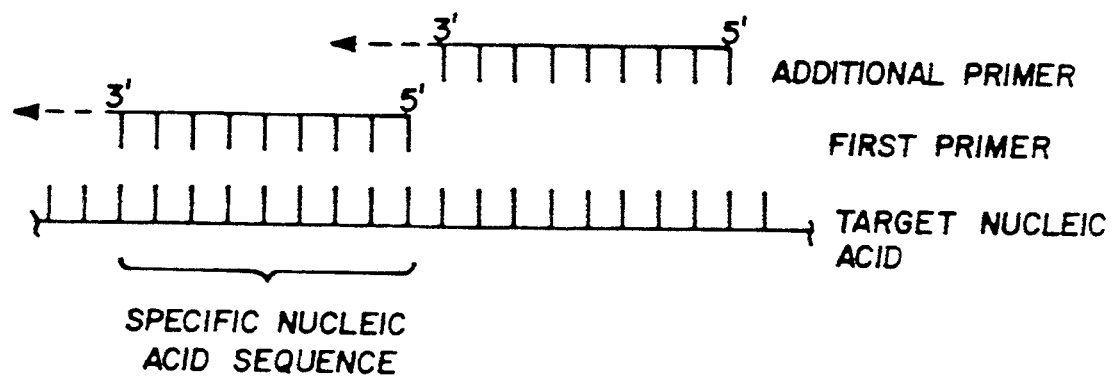
FIG. 4 is a schematic diagram showing still another embodiment of this invention as described in more detail on page 13 below.

In FIG. 4, an embodiment of category (ii), noted above, is illustrated wherein the additional primer is complementary to a nucleic acid sequence "immediately adjacent" the sequence for the first primer. As noted in the illustration, this means that the 3' end of the additional primer has a base complementary with the base of the target sequence which is one base removed from the base complementary with the 5' end of the first primer. More than one additional primer can be used (not illustrated) as long as they all have the same base at the 3' end.

Figure 5:
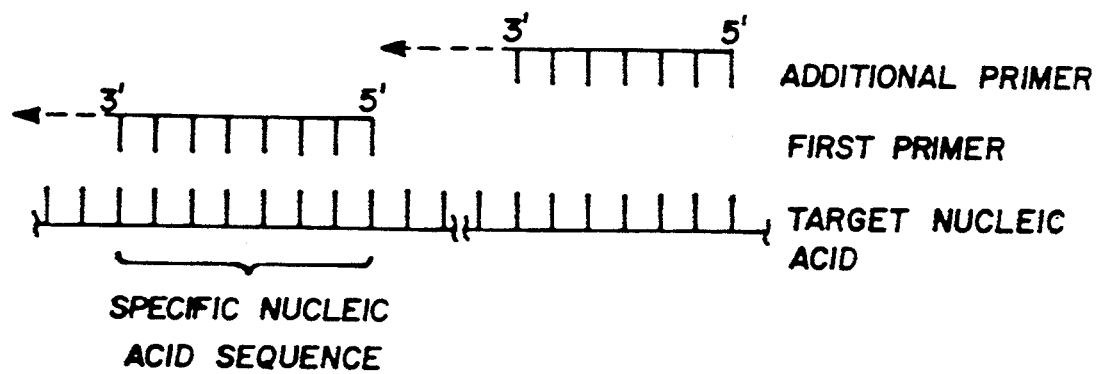
FIG. 5 is a schematic diagram showing yet another embodiment of this invention as described in more detail on page 13 below.

FIG. 5 illustrates a further embodiment which falls into category (iii), noted above. The one or more additional primers are complementary to a nucleic acid sequence(s) which is removed from the first sequence by one or more bases. But at least one of these additional primers, even if removed by several bases, is still capable of forming a primer extension product complementary to the first nucleic acid sequence. Generally, this means that at least one of the additional primers would be complementary to a nucleic acid sequence which is less than about 50 kilodaltons removed from the nucleic acid sequence of the first primer. Selection of the additional primers might require some routine experimentation to find those which would form extension products over the suspected mismatch. Such experimentation, however, would be well within the purview of a worker skilled in the art. In FIG. 5, the double break lines are intended to indicate that the additional primer is removed by more than the three bases specifically shown.

Figure 6:
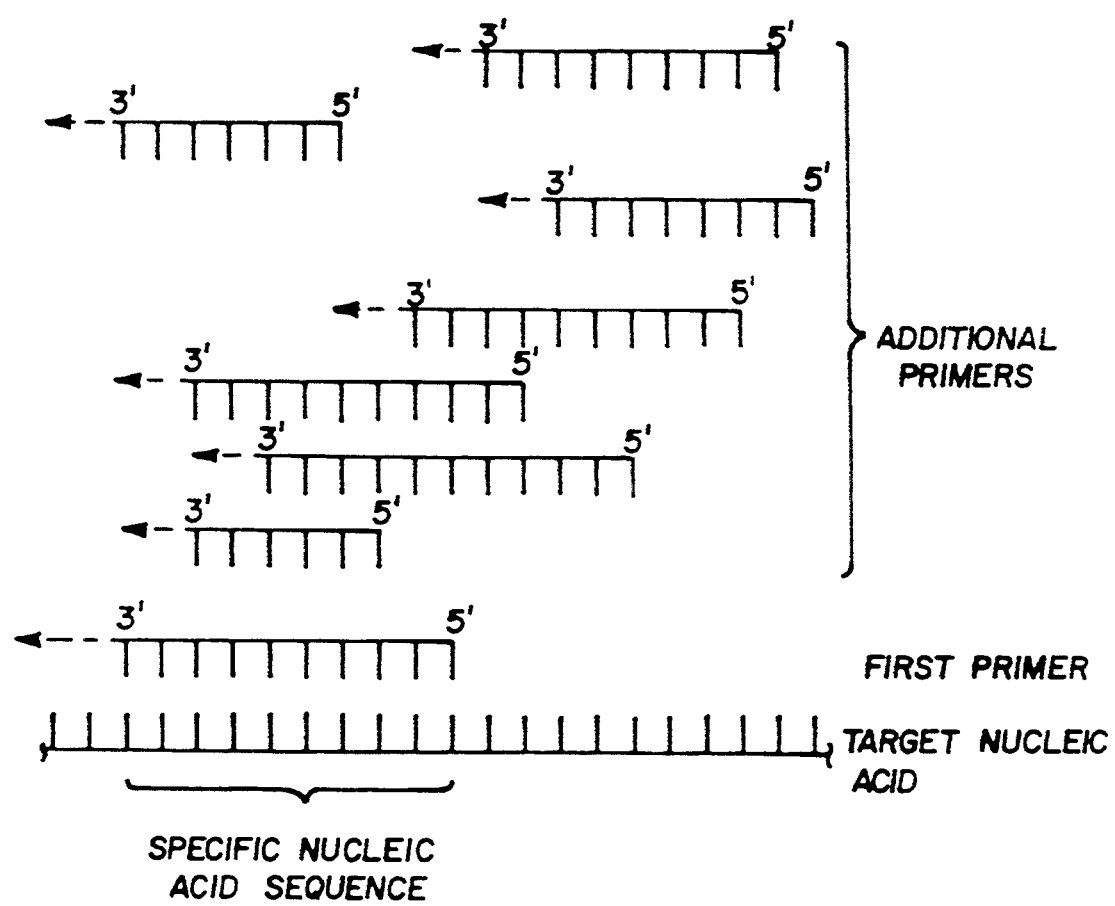
FIG. 6 is a schematic diagram showing still another embodiment of this invention as described in more detail on pages 13 and 14 below.

In FIG. 6, an embodiment is illustrated which utilizes additional primers from all three categories (i)–(iii), noted above. Some of the additional primers are complementary to a nucleic acid sequence which overlaps a portion of the first sequence, while one illustrated primer has an "adjacent" sequence, and still another has a sequence removed by three bases. Other mixtures of additional primers could be designed and used with the teaching herein.

Preferred compositions of this invention are like those illustrated in either FIGS. 2 or 3.

In the composition and methods of the present invention, the concentrations of each of the first and additional primers can be varied from 0.001 to 99.999 molar percent. The exact concentrations of the primers in the composition would be varied depending upon the particular relationship of the primers. For example, it is preferred that for the composition illustrated in FIG. 2, the shortest primer be present in the greatest concentration. Thus, even if the larger primer effectively form extension products, the shorter primers will be available for later amplification cycles, and the efficiency of the process is further improved. In other embodiments, generally, the primers are present in equal concentration.

The composition of the present invention is useful for replication of a predetermined target nucleic acid. The first step of such a procedure is to prepare a specimen containing the target nucleic acid for replication. This usually means removing unwanted proteins and cellular matter from the specimen in a suitable manner. Various procedures are known in the art, including those described by Laure et al in *the Lancet*, pp. 538–540 (Sept. 3, 1988) and by Gross-Belland et al in *Eur.J.BioChem.*, 36, 32 (1973).

Once the specimen has been prepared, it is contacted with the composition of this invention under conditions such that a mixture of hybridized products of primers and target nucleic acid are formed. Such conditions are those normally used for amplification as described in U.S. Pat. No. 4,683,202 (noted above). Then, primer extension products are formed with at least one of the hybridized products followed by additional priming and extension product formation. After denaturation (that is, separation of complementary products), the replicated target nucleic acid can be isolated from the reaction mixture using standard procedures and equipment.

In a preferred embodiment, replication includes further amplification of the target nucleic acid using a polymerase chain reaction (described in more detail below). Replication of a target nucleic acid may be useful for preparation of genes or gene fragments or for sequencing genomic DNA.

The present invention is also useful for detection of a specific nucleic acid having two complementary strands. Most nucleic acid sequences of interest already are double-stranded, such as those found in DNA. However, single-stranded nucleic acid sequences, such as mRNA, can be similarly detected after it is converted to a double-stranded sequence using reverse transcriptase.

A specific nucleic acid sequence is produced using the nucleic acid containing that sequence as a template. If the acid contains two strands, it is necessary to separate the strands, either as a separate step or simultaneously with the formation of primer extension products. Denaturing can be accomplished using any suitable physical, chemical or enzymatic means as described in the art. Heating to a suitable temperature is a preferred means.

Once the separated strands are available for use, synthesis of additional nucleic acid strands can be carried out using the primer composition of this invention in a buffered aqueous solution generally at a pH of from about 7 to about 9. A primer for the complementary DNA strand can also be included. Preferably, a molar excess of the primers is added to the buffered solution, and specific amounts are taught in the art (for example, U.S. Pat. No. 4,683,202, noted above). The deoxyribonucleoside triphosphates dATP, dCTP, dGTP and dTTP are also added to the synthesis mixture in adequate amounts and the resulting solution is heated to about 90°–100° C. for up to 10 minutes, and preferably from about 1 to about 4 minutes. After this heating, the solution is preferably cooled to room temperature, and an appropriate agent for inducing (or catalyzing) the formation of primer extension products is introduced. This inducing agent is generally known in the art as a polymerization agent. Reaction to form these products is carried out under known conditions (generally from room temperature to that temperature at which polymerization no longer occurs).

The polymerization agent may be any compound, or combination of reagents, which will function to accomplish the synthesis of primer extension products, including enzymes (for example, *E. coli* DNA polymerase I, T4 DNA polymerase, Klenow polymerase, reverse transcriptase and others known in the art). Particularly useful enzymes are thermally stable enzymes, cloned or naturally occurring, such as those obtained-from various Thermus bacterial species. Other polymerization agents are described in U.S. Pat. No. 4,683,202 (noted above), incorporated herein by reference.

Preferred thermal-stable enzymes are DNA polymerases from *Thermus aquaticus* as described in U.S. Ser. No. 063,647 (filed Jun. 17, 1987 by Mullis et al), U.S. Pat. No. 4,965,188 and E.P. Publication 258,017 (published Mar. 2, 1988). Those polymerases generally have a molecular weight of about 86,000–90,000 daltons. Other useful enzymes are described by Rossi et al, *Syst. Appl. Microbiol,* 7(2–3), pp. 337–341, 1986. Many useful polymerases are commercially available. Generally, the synthesis of extension products will be initiated at the 3' end of each primer and proceed in the 5' to 3' direction along the template until synthesis is terminated. Some polymerization agents (for example, reverse transcriptase) may proceed in the 3' to 5' direction along the template.

The newly formed primer extension products comprising the newly synthesized strands and their respective primers form double-stranded molecules with the initial target strands which are used in the succeeding steps of the method. These strands are then separated by denaturation as described above to provide single-stranded molecules, onto which new nucleic acids are synthesized as described above. Additional reagents may be needed to keep the amplification procedure going, after which most of the extension products will consist of the specific nucleic acid sequence bounded by the primers (that is, complementary products).

The steps of strand separation and extension product synthesis can be repeated as often as needed to produce the desired quantity of the specific nucleic acid needed for the use, for example detection. Generally, the sequence of steps is repeated at least once, and preferably at least 10 to 50 times.

When it is desired to produce more than one specific nucleic acid from the first nucleic acid or a mixture thereof, the appropriate number of sets of primers are used in the general procedure described above.

At any point in the method of this invention after the generation of at least one primer extension product, that product can be hybridized with a detectably labeled probe (described below). This contact of probe and extension product can occur at any appropriate time during the method.

Generally, once a desired amount of the nucleic acid sequence of interest has been generated and the primer extension products are separated for a last time, the first primer extension product (that is, the one formed using the primer composition of this invention) is contacted with an oligonucleotide probe which is labeled for detection and is complementary thereto to form a product. The probe is a nucleic acid sequence which is complementary with the target nucleic acid sequence. The probes can be of any suitable length of nucleic acids, but preferably, they have from about 15 to about 40 nucleic acids. They are labeled (commonly at the 5' end) with any suitable detectable material(either directly or indirectly). Procedures for attaching labels and preparing probes are well known in the art, for example, as described by Agrawal et al, *Nucleic Acid Res.,* 14, pp. 6227–45 (1986), and in the references noted above for attaching a specific binding ligand to a primer. Useful labels include radioisotopes, electron-dense reagents, chromogens, fluorogens, phosphorescent moieties, ferritin and other magnetic particles, chemiluminescent moieties and enzymes (which are preferred). Useful enzymes include, glucose oxidase, peroxidase, uricase, alkaline phosphatase and others known in the art. Substrates and dye forming compositions for such enzymes are well known. The labeled primers described in U.S. Ser. No. 076,394 abandoned (noted above) can also be used as probes in the practice of this invention.

In a particularly preferred embodiment, the label is peroxidase, and at some point in the assay, hydrogen peroxide and suitable dye-forming compositions are added to provide a detectable dye. For example, useful dye-providing reagents include tetramethylbenzidine and derivatives thereof, and leuco dyes, such as triarylimidazole leuco dyes (as described in U.S. Pat. Nos. 4,089,747, issued May 16, 1978 to Bruschi), or other compounds which react to provide a dye in the presence of peroxidase and hydrogen peroxide. Particularly useful dye-providing compositions are described in PCT Applications 88/02806 (of Bloch) and 88/02807 (of Bloch etal), both filed Aug. 16, 1988 and U.S. Ser. No. 136,166 (filed Dec. 18, 1987 by McClune et al) U.S. Pat. No. 5,024,935.

Detection of the presence of the probe which is in the complementary product can be achieved using suitable and known detection equipment and procedures. Certain probes may be visible to the eye without the Use of detection equipment. It is also useful for the method to be carried out in a suitable container. The most crude container would be a test tube, flask or beaker, but more sophisticated containers have been fashioned in order to facilitate automated procedures for performing the method. For example, a cuvette constructed to provide certain temperature characteristics during the practice of the method is described and claimed in copending U.S. Ser. No. 273,781 U.S. Pat. No. 4,902,629 filed on Nov. 21, 1988 by Burdick, Columbus, Helfer, Porte and Wellman and entitled "Cuvette" which is a continuation of U.S. Ser. No. 270,385 abandoned (filed on Nov. 9, 1988 by Columbus, Helfer, Porte and Wellman) which is also entitled "Cuvette", which in turn is a Continuation-in-part of U.S. Ser. No. 123,751, filed Nov. 23, 1987 abandoned. Other useful containers could be suitably fashioned for automated or single use of the method of this invention.

In order for the probe in the complementary product to be detected, it is often important for the complementary product to be separated from the other materials in the reaction medium. This is done by any of a number of ways, including using a capture means on a primer so that the primer extension products which are replicated in the method and to which the probe is attached, are removed from the reagent mixture. Primers can be attached to insoluble materials in a suitable manner, or they can be designed to be capturable, that is, reactive with a capture means at some point in the method.

One useful capture means is described in U.S. Ser. No. 273,779 filed on Nov. 21, 1988 by Burdick et al abandoned. A primer has a specific binding ligand attached thereto (such as biotin, an antibody or a lectin) which is capable of specifically binding to a receptor molecule (such as avidin, an antigenic material or a sugar) which is bound in a suitable manner to an insoluble material. Further details can be obtained by consulting that application. The resulting insolubilized complexed product can be separated from uncomplexed materials by filtration, centrifugation or other suitable separation techniques.

Particularly useful separation means are microporous filter membranes such as the polyamide membranes marketed by Pall Corp. (for example as Loprodyne ™ or Biodyne ™ membranes). They can be used uncoated or precoated with surfactants or other materials which facilitate the analytical procedures.

The membranes can be used as a separate substrate with suitable containers for carrying out other steps of the assay. Preferably, however, they are mounted as part of a test device. Various test devices are known in the art including those described in U.S. Pat. Nos. 3,825,410 (issued Jul. 23, 1974 to Bagshawe), 3,888,629 (issued Jun. 10, 1975 to Bagshawe), 3,970,429 (issued Jul. 20, 1976 to Updike) and 4,446,232 (issued May 1, 1984 to Liotta). Particularly useful devices are described in copending U.S. Ser. No. 98,248 (filed Sep. 18, 1987 by Hinckley et al) abandoned.

Any useful solid support can be used for separation of product for detection, including a microtiter plate, test tube, beaker, beads, film, membrane filters, filter papers, gels, magnetic particles or glass wool. It can be made of a number of materials including glass, ceramics, metals, naturally occurring or synthetic polymers, cellulosic materials, filter materials and others readily apparent to one of ordinary skill in the art. Particularly useful solid support materials are polymeric beads generally having an average particle size of from about 0.1 to about 10 $\mu$meters. Further details about such preferred polymeric particles, including useful monomers, methods of preparing them and attachment of receptor molecules, are provided in copending U.S. Ser. No. 136,165, filed Dec. 18, 1987 by Sutton et al.

The method described herein can be used to provide the detection or characterization of specific nucleic acid sequences associated with infectious diseases, genetic disorders or cellular disorders such as cancers. It may also be used in forensic investigations and DNA typing. For purposes of this invention, genetic diseases include specific deletions or mutations in genomic DNA from any organism, such as sickle cell anemia, cystic fibrosis, $\alpha$-thalassemia, $\beta$-thalessemia and others readily apparent to one skilled in the art. The presence of Human Leukocyte Antigen (HLA) can be detected with the present invention. Various infectious diseases can be diagnosed by the presence in a clinical sample of small quantities of specific DNA sequences characteristic of the organism, whether it be a yeast, bacterium or virus. Such bacteria which can be detected include, but are not limited to, Salmonella, Chlamydia, Gonorrhea, Shigella and Listeria. Viruses which are detectable include, but are not limited to, herpes, Epstein Bart virus, cytomegalovirus, hepatitis and retroviruses such as HTLV-I and HIV-I. Protozoan parasites, yeasts and molds are also detectable. Other detectable species would be readily apparent to one skilled in the art. The invention is particularly useful for the detection of the presence of retroviruses, such as HIV-I, in test samples, by detecting the presence of vital DNA.

The diagnostic test kit of this invention has been generally described above. Critical components in the kit include the first oligonucleotide primer, and the one or more additional primers described above. The kit may contain a set of primers for each nucleic acid sequence of interest.

Preferably, the kit also contains an agent for primer polymerization such as a DNA polymerase (such as a polymerase obtained from *Thermus aquiticus*), the four different deoxyribonucleoside triphosphates (dATP, dCTP, dGTP and dTTP), a detectable probe, a dye providing composition where the probe is labeled with an enzyme or an insoluble substrate as described herein, all generally in separate containers.

The kit components are packaged in a suitable manner, and can be included with a number of optional components such as pipettes, cuvettes, instructions, buffers, wash solutions, diluents and other reagents, materials and equipment which may be useful in practicing the present invention. These additional components are well known in the art.

The following examples are included to illustrate the practice of this invention, and are not meant to be limiting in any way.

The DNA polymerase used in Example 2 was obtained commercially. It had been isolated from *Thermus aquaticus* and had an activity of 2.5 units/$\mu$l where 1 unit represents the amount needed to incorporate 10 mmolar of dNTP into a primer extension product in 30 minutes at 74° C.

The "running buffer" (pH 8) used for electrophoresis was composed of tris(hydroxymethyl)aminomethane (89 mmolar), boric acid (89 mmolar) and ethylenediaminetetraacetic acid (2 mmolar).

Sample Preparation

A whole blood sample (100 $\mu$l) taken from a patient suspected of carrying the HIV-I virus, was added to a test tube containing an aqueous dextran solution (250 $\mu$l, 3 weight % dextran having 24,000 molecular weight), and mixed by inverting the test tube several times. After five minutes at room temperature, the supernatant was poured into another test tube and heated for 5 minutes at 100° C. The mixture was then centrifuged for seconds and the supernatant (50 $\mu$l aliquots) was transferred to another test tube, ready for use in amplification. This procedure extracted the targeted vital DNA as described in more detail in copending U.S. Ser. No. 339,437 (filed on even date herewith by Burdick et al and entitled "Methods of Extracting, Amplifying and Detecting a Nucleic Acid from a Biological Specimen"), now abandoned in favor of CIP U.S. Ser. No. 406,222 (filed Sep. 12, 1989).

Example 1: Primer Compositions for HIV-I DNA Detection

Two primer compositions of this invention were prepared as described below for use in Example 2. The compositions consisted of two sets of five primers each.

Two sets of five primers each were prepared for the two strands of the target DNA. The homologous primer sets are identified below as A, $A_1$, $A_2$, $A_3$ and $A_4$, and B, $B_1$, $B_2$, $B_3$ and $B_4$. The sequences of the A and B primers were obtained from Laure et al of the Lancet, (noted above). As is standard in the art, the sequences are identified by letters identifying the individual nucleotide bases, that is adenine(A), thymine(T), guanine(G) and cytosine(C). The primers had the following nucleotide sequences:

Primer A (+), 25 bases: 5'-TGGGAAGTTCAAT-TAGGAATACCAC-3'

Additional Primers (+):

$A_1$, 24 bases: 5'-TGGGAAGTTCAATTAG-GAATACCA-3'

$A_2$, 23 bases: 5'-TGGGAAGTTCAATTAG-GAATACC-3'

A3, 22 bases: 5'-TGGGAAGTTCAATTAG-GAATAC-3'

A4, 21 bases: 5'-TGGGAAGTTCAATTAG-GAATA-3'

Primer B (-), 26 bases: 5'-CCTACATACAAAT-CATCCATGTATTC-3'

Additional Primers (−):

B1, 25 bases: 5'-CCTACATACAAATCATC-CATGTATT-3'

B2, 24 bases: 5'-CCTACATACAAATCATC-CATGTAT-3'

B3, 23 bases: 5'-CCTACATACAAATCATC-CATGTA-3'

B4, 22 bases: 5'-CCTACATACAAATCATC-CATGT-3'

The primers were prepared using the following procedures:

Automated Synthesis Procedure

The diisopropylphosphoramidites (obtained from American Bionetics) were sequentially condensed to a nucleotide derivatized controlled pore glass support (obtained from Bioscatch) using a Biosearch 8700 DNA Synthesizer from Milligen/Biosearch.

The procedure included detritylation using dichloracetic acid in dichloromethane, condensation using 5-methylthiotetrazole as activating proton donor and capping with acetic anhydride and N-methylimidazole/pyridine in tetrahydrofuran. The cycle time was about 6 minutes. The yields at each step were greater than 98% and were determined by collection and spectroscopic examination of the dimethyoxytrityl alcohol released during detritylation.

Oligonucleotide Deprotection and Purification Procedures

The solid support was removed from the column and exposed to 2 ml of concentrated ammonium hydroxide at 55° C. for 6–18 hours. The support was then removed by filtration and the ammonia solution was evaporated to 1 ml by allowing nitrogen to flow over the solution.

The sample (in 0.1 molar triethylamine acetate buffer, pH 6.9) was passed through a NAP-10 column (Pharmacia AB), then purified further by HPLC using a PRP-1 column (Hamilton Co.) with the standard trityl on/trityl off method as described in the Biosearch product literature, or used directly after detritylation. Removal of the trityl groups was accomplished with 100 mmolar acetic acid for 1 hour at 20°–25° C., followed by neutralization with triethylamine and a second pass through a HAP-10 column.

Characterization of Oligonucleotides

Base composition was determined by digestion of the oligodeoxyribonucleotide to component nucleotides using snake venom phosphodiesterase, followed by separation and quantitation of the derived nucleotides using a reverse phase HPLC column and an acetonitrile/ammonium acetate mobile phase.

Example 2: Detection Of HIV-I Target DNA

The present invention was demonstrated using the primer compositions of Example 1 in the amplification and detection of targeted HIV-I viral DNA. The invention was compared to an attempt to detect the same target using only Primers A and B.

The following Test amplification solution (100 pl) was prepared:

A buffered solution containing tris(hydroxymethyl-)aminomethane hydrochloride buffer (pH 8, 10 mmolar) and magnesium chloride (10 mmolar) was mixed with a solution (2 µl) containing the primer compositions (+and −) described above (100 µmolar with 10% each of Primers A, $A_1$, $A_2$ and $A_3$ and 60% Primer $A_4$, and similarly for the B primer composition), and the deoxynucleotide triphosphates (dNTP, 1500 µmolar each). The DNA target (0.1 µmolar) was then added, followed by the DNA polymerase (2.5 units).

The Test and Control (only Primers A and B) solutions were individually put into microcentrifuge tubes and polymerase chain reactions were carried out for 30 consecutive cycles as described below:

Heated to 94° C. over 1 minute,
Maintain for 30 seconds,
Lower temperature to 50° C. over 80 seconds,
Maintain for 30 seconds,
Raise temperature to 70° C. over 45 seconds, and
Maintain for 1 minute.

Aliquots (5 µl) were withdrawn and applied to 4% agarose gels (3% NuSieve ™ and 1% SeaKem ™, available from FMC BioProducts). The gels were prestained with 4 µl of an ethidium bromide aqueous solution (10 mg/ml). The "running buffer" (600 µl) contained 24 µl ethidium bromide. The gels were electrophoresed at 160 volts/cm for 1 hour, then photographed and the resulting bands visualized.

The Test mixture containing the primer compositions of this invention gave highly visible bands in the gel. The Control mixture (containing only Primers A and B) provided no observable bands in the gel.

The invention has been described in detail with particular reference to preferred embodiments thereof, but it will be understood that variations and modifications can be effected within the spirit and scope of the invention.

I claim:

1. A primer composition useful for amplification or replication of a predetermined single-stranded target nucleic acid, said composition comprising an aqueous mixture of:
   a) a first oligonucleotide primer which is substantially complementary to and hybridizable with a first specific nucleic acid sequence of said single-stranded target nucleic acid, and
   b) at least one additional oligonucleotide primer which is at least substantially complementary to and hybridizable with an additional nucleic acid sequence of said single-stranded target nucleic acid, wherein said additional nucleic acid sequence of said single-stranded target nucleic acid is either:
      i) inclusive of only a portion of said first nucleic acid sequence, and each of said additional oligonucleotide primers being shorter than said first oligonucleotide primer, and the bases at the 5' end of said first and additional primers are identical, or
      ii) inclusive of only a portion of said first nucleic acid sequence, and each of said additional oligonucleotide primers is of the same length as said first oligonucleotide primer, and each of said additional oligonucleotide primers overlaps said first oligonucleotide primer by at least one base.

2. The composition of claim 1 wherein said first and additional primers are substantially complementary to a vital DNA strand.

3. The composition of claim 2 wherein said first and additional primers are substantially complementary to a HTLV-I or HIV-I vital DNA strand.

4. The composition of claim 1 having from to 10 additional primers.

5. The composition of claim 1 wherein said additional primers have the same length as said first primer, but each additional primer being substantially complementary to and hybridizable with a portion of said first nucleic acid sequence, and said additional primers being shifted from each other by a single nucleotide base.

6. The composition of claim 1 wherein said additional primers have less than the number of nucleotide bases as said first primer, vary in length from each other by two bases, and the bases at the 5' end of said first and additional primers are the same.

7. A diagnostic test kit useful for amplification or replication of a predetermined single-stranded target nucleic acid, said kit comprising:
  a) a first oligonucleotide primer which is substantially complementary to and hybridizable with a first specific nucleic acid sequence of said single-stranded target nucleic acid,
  b) at least one additional oligonucleotide primer which is at least substantially complementary to and hybridizable with an additional nucleic acid sequence of said single-stranded target nucleic acid, wherein said additional nucleic acid sequence of said single-stranded target nucleic acid is either:
    i) inclusive of only a portion of said first nucleic acid sequence, and each of said additional oligonucleotide primers being shorter than said first oligonucleotide primer, and the bases at the 5' end of said first and additional primers are identical, or
    ii) inclusive of only a portion of said first nucleic acid sequence, and each of said additional oligonucleotide primers is of the same length as said first oligonucleotide primer, and each of said additional oligonucleotide primers overlaps said first oligonucleotide primer by at least one base, and
  c) a DNA polymerase.

8. The kit of claim 7 wherein said polymerase is obtained from *Thermuis aquaticus*.

9. The kit of claim 7 further comprising four different deoxyribonucleoside triphosphates.

10. The kit of claim 7 further comprising a detectable probe complementary to said target nucleic acid.

11. The kit of claim 10 wherein said probe is labeled with an enzyme.

12. The kit of claim 11 wherein said enzyme is peroxidase.

13. The kit of claim 11 further comprising a composition which provides a dye in the presence of said enzyme.

14. The kit of claim 7 wherein at least one of said primers is attached to or capable of being attached to an insoluble substrate, said attachment being at one end of said primer.

15. The kit of claim 14 wherein said substrate is a polymeric particle.

16. A method for the replication of a predetermined single-stranded target nucleic acid, said method comprising:
  A. preparing a specimen containing said predetermined single-stranded target nucleic acid for replication, and
  B. contacting said prepared specimen with a primer composition comprising an aqueous mixture of:
    a) a first oligonucleotide primer which is substantially complementary to and hybridizehie with a first specific nucleic acid sequence of said singles-tranded target nucleic acid, and
    b) at least one additional oligonucleotide primer which is at least substantially complementary to and hvbridizable with an additional nucleic acid sequence of said single-stranded target nucleic acid, wherein said additional nucleic acid sequence of said single-stranded target nucleic acid is either:
      i) inclusive of only a portion of said first nucleic acid sequence, and each of said additional oligonucleotide primers being shorter than said first oligonucleotide primer, and the bases at the 5' end of said first and additional primers are identical,
      ii) inclusive of only a portion of said first nucleic acid sequence, and each of said additional oligonucleotide primers is of the same length as said first oligonucleotide primer, and each of said additional oligonucleotide primers overlaps said first oligonucleotide primer by at least one base, or
      iii) immediately adjacent to said first nucleic acid sequence,
  so as to form a mixture of hybridized products of said primers and said single-stranded target nucleic acid, and
  C. forming a first primer extension product of at least one of said hybridized products thereby resulting in replication of said predetermined single-stranded target nucleic acid.

17. The method of claim 16 further comprising the step of amplifying said first primer extension product.

18. The method of claim 17 wherein said amplification is carried out using a polymerase chain reaction.

19. A method for the detection of a predetermined single-stranded target nucleic acid, said method comprising:
  A. contacting a specimen suspected of containing said single-stranded target nucleic acid with a primer composition comprising an aqueous mixture of:
    a) a first oligonucleotide primer which is substantially complementary to and hybridizable with a first specific nucleic acid sequence of said single-stranded target nucleic acid, and
    b) at least one additional oligonucleotide primer which is at least substantially complementary to and hybridizable with an additional nucleic acid sequence of said single-stranded target nucleic acid, wherein said additional nucleic acid sequence of said single-stranded target nucleic acid is either:
      i) inclusive of only a portion of said first nucleic acid sequence, and each of said additional oligonucleotide primers being shorter than said first oligonucleotide primer, and the bases at the 5' end of said first and additional primers are identical,
      ii) inclusive of only a portion of said first nucleic acid sequence, and each of said additional oligonucleotide primers is of the same length as said first oligonucleotide primer, and each of said additional oligonucleotide primers overlaps said first oligonucleotide primer by at least one base, or
      iii) immediately adjacent to said first nucleic acid sequence, so as to form a mixture of hybridized products of said primers and said single-stranded target nucleic acid, B. forming a first primer extension product of at least one of said hybridized products, and amplifying said first primer extension product using polymerase chain reaction, C. denaturing the resulting primer extension products and contacting them with a detectable oligonucleotide probe to form a detectable complementary product, and D. determining said detectable complementary product as an indication of the presence of said single-stranded target nucleic acid in said specimen.

20. The method of claim 19 wherein said single-stranded target nucleic acid is a strand of HLA DNA.

21. The method of claim 19 wherein said single-stranded target nucleic acid is a strand of a retroviral DNA.

22. The method of claim 21 wherein said single-stranded target nucleic acid is a strand of HTLV-I or HIV-I DNA.

23. The method of claim 19 carried out using from 1 to 10 additional primers.

24. The method of claim 19 wherein said additional primers have the same length as said first primer, but each additional primer being substantially complementary to and hybridizable with a portion of said first nucleic acid sequence, and said additional primers being shifted from each other by a single nucleotide base.

25. The method of claim 19 wherein said additional primers have less than the number of nucleotide bases as said first primer, vary in length from each other by two bases, and the bases at the 5' end of said first and additional primers are the same.

26. The method of claim 19 wherein said amplification is carried out using a polymerase from *Thermus aquaticus*.

27. The method of claim 19 wherein said probe is enzyme labeled.

28. The method of claim 19 wherein said probe is enzyme labeled.

29. The method of claim 28 wherein said enzyme is peroxidase, and said detection is carried out using a composition which provides a dye in the presence of peroxidase and hydrogen peroxide.

30. The method of claim 29 wherein said dyeproviding composition comprises a triarylimidazole leuco dye.

31. The method of claim 20 wherein one of said primers is attached to an insoluble substrate, said attachment being at one end of said primer.

32. The method of claim 31 wherein said substrate is a polymeric particle.

* * * * *